(12) United States Patent
Berkelmans (10) Patent No.: US 7,293,623 B2
(45) Date of Patent: Nov. 13, 2007

(54) ASSEMBLY OF A WHEELCHAIR AND A RECLINING CYCLE

(76) Inventor: Henricus Wilhelmus A. Berkelmans, Zuid Willemsvaart 241G, 's-Hertogenbosch (NL) 5211 SH ( * ) Notice: Subject to any disclaimer, the term of this patent is extended or adjusted under 35 U.S.C. 154(b) by 0 days.

(21) Appl. No.: 10/398,082

(22) PCT Filed: Oct. 2, 2001

(86) PCT No.: PCT/NL01/00720

§ 371 (c)(1),
(2), (4) Date: Aug. 1, 2003

(87) PCT Pub. No.: WO02/28700

PCT Pub. Date: Apr. 11, 2002

(65) Prior Publication Data

US 2004/0026891 A1      Feb. 12, 2004

(30) Foreign Application Priority Data

Oct. 2, 2000     (NL) .................................. 1016310

(51) Int. Cl.
*B62M 1/14* (2006.01)
*B62K 17/00* (2006.01)

(52) U.S. Cl. ................ 180/205; 180/304.1; 180/226.1; 180/280.1; 180/288.1; 180/230; 180/233; 180/234; 297/DIG. 16.4

(58) Field of Classification Search ................ 280/224, 280/225, 226.1, 233, 234, 250, 250.1, 304.1, 280/288.1; 297/DIG. 4
See application file for complete search history.

(56) References Cited

U.S. PATENT DOCUMENTS

| 4,152,005 A | * | 5/1979 | Vanore ........................ 280/234 |
| 4,421,336 A | | 12/1983 | Petrofsky et al. |
| 4,572,501 A | | 2/1986 | Durham et al. |
| 4,705,284 A | * | 11/1987 | Stout ........................ 280/250.1 |
| 4,720,117 A | * | 1/1988 | Hay ........................... 280/250 |
| 5,242,179 A | | 9/1993 | Beddome et al. |
| 5,324,060 A | * | 6/1994 | Van Vooren et al. .... 280/304.1 |
| 5,501,480 A | | 3/1996 | Ordelman et al. |
| 5,899,476 A | * | 5/1999 | Noyola ..................... 280/250.1 |
| 6,092,822 A | * | 7/2000 | Salmon ....................... 280/261 |
| 6,106,440 A | * | 8/2000 | Olbrish, Jr. .............. 280/304.1 |
| 6,276,703 B1 | * | 8/2001 | Caldwell .................. 280/242.1 |

FOREIGN PATENT DOCUMENTS

| DE | 94 20 328.8 | 2/1995 |
| EP | 0 339 665 | 4/1989 |
| JP | 2-57255 | 2/1990 |
| JP | 2-83185 | 6/1990 |
| WO | 97/23189 | 7/1997 |

* cited by examiner

*Primary Examiner*—Lesley D. Morris
*Assistant Examiner*—Marlon Arce-Diaz
(74) *Attorney, Agent, or Firm*—Merchant & Gould P.C.

(57) ABSTRACT

An assembly comprising a wheelchair and a reclining cycle part which are connectible to each other with the aid of a coupling, the reclining cycle part comprising a wheel and at least one pedal with which the wheel is drivable, so that the assembly in a coupled condition in use can be propelled by a person present in the wheelchair with the aid of a cycling motion of a leg making contact with the pedal, the reclining cycle part being further provided with a handlebar which is connected with the wheel of the reclining cycle part for steering the assembly, the assembly being provided with an electric energy source for electrostimulation, in use, of the cycling motion at the at least one leg of the person present in the wheelchair.

5 Claims, 6 Drawing Sheets

ASSEMBLY OF A WHEELCHAIR AND A RECLINING CYCLE

The invention relates to an assembly comprising a wheelchair and a reclining cycle part which are connectible to each other with the aid of a coupling, the reclining cycle part comprising a wheel and at least one pedal with which the wheel is drivable, so that the assembly in a coupled condition in use can be propelled by a person present in the wheelchair with the aid of a cycling motion of a leg making contact with the pedal, the reclining cycle part being further provided with a handlebar which is connected with the wheel of the reclining cycle part for steering the assembly. Such an assembly is known from U.S. Pat. No. 5,324,060.

In this known assembly, a wheelchair is coupled to a cycle, and a set of pedals is placed adjacent a front wheel, so that these pedals can be used by person sitting in the wheelchair to move the legs to thereby prevent muscular atrophy. The drive and the handlebar are adapted to facilitate the use of the assembly.

A drawback of this known assembly is that by a person with very weak leg muscles, such as, for instance, a paraplegic with paralyzed legs, the assembly cannot be driven and that therefore the legs cannot be moved to prevent muscular atrophy.

An object of the invention is to meet this drawback.

This object is achieved with the assembly according to the invention, which is characterized in that the assembly is provided with an electric energy source for electrostimulation, in use, of the cycling motion adjacent at least one leg of the person present in the wheelchair. This provides the advantage that the at least one leg that performs the cycling motion drives the wheel of the reclining cycle part, whereby the assembly can be advanced. Preferably, if possible, both legs are set into motion with the aid of electrostimulation. Through the cycling motion, muscular atrophy in the legs can be prevented. In addition, the assembly provides the possibility to a person with wholly or partly paralyzed legs, to travel not only by driving the wheelchair wheel through arm force or motor force, but also by cycling. Once having arrived at a destination, the user of the assembly can uncouple the reclining cycle part and proceed to park in the wheelchair or to travel further with the aid of the wheelchair alone.

An embodiment of the assembly according to the invention is characterized in that the assembly is further provided with a separate drive which is coupled with an axle of the wheelchair, coupled with the wheelchair wheels, or with the wheel of the reclining cycle part. This provides the advantage that a forward movement can be set going through the separate drive. When applying the feet to the pedals and starting up the cycling motion of the legs with the aid of the separate drive, the joints in the legs are already 'lubricated' to some extent before the legs drive the wheel of the reclining cycle part with the aid of electrostimulation. Moreover, a deficit of driving power produced by the legs is compensated by the separate drive. When the legs can produce more driving power, optionally the use of the separate drive can be discontinued. The separate driving power can comprise an electric motor. An alternative separate driving power comprises a hand- or arm-drive fitted on the handlebar.

In a particular embodiment, it holds that the hand- or arm-drive is provided with at least one manually drivable pedal which, via a drive shaft, with the aid of a belt or a chain, is coupled with at least one hub or gear wheel which is connected with the axle of the wheelchair coupled to the wheelchair wheels. The chain or belt can be coupled, via a derailleur or a speed-changing gear with a differential, to the wheelchair axle coupled with the wheelchair wheels. It is further possible that the wheel of the reclining cycle part is steerable with the aid of a tilting of the handlebar over an axis located substantially parallel to a direction of travel and a ground surface, the tilt being convertible, with the aid of a system of rods, into a rotation of the wheel about a substantially upwardly directed axis.

In an alternative embodiment, it holds that the hand- or arm-drive is provided with at least one manually drivable pedal with which, via a drive shaft, with the aid of a chain or a belt, the wheel of the reclining cycle part is drivable. The front wheel in such an embodiment can be steerable by turning the hand- or arm-drive about a steering axis.

The reclining cycle part is preferably provided with an asymmetrical front fork for providing space to the belt or chain when the wheel is changed in direction.

A further elaborated embodiment of an assembly according to the invention is provided with a computer for operatively controlling the electrostimulation of the cycling motion.

A very special embodiment of an assembly according to the invention is characterized in that the assembly is provided with electrodes which form a part of a system of Functional ElectroStimulation (FES), whereby in use leg muscles are controllable via a current supplied by the electrodes and originating from the electric energy source, while the reclining cycle part is provided with a pedal angle gauge which transmits a position of the at least one pedal relative to a crank axle to the computer in order to perform, on the basis of that position, an electrostimulation on the leg muscles according to a predetermined protocol. FES is a proven method, whereby control of the muscles takes place by passing an electrical current through the muscles, so that the muscle contracts at the desired moment. In this embodiment, the control of the electrodes can take place in an effective manner. In other words, a leg which is to perform an extending motion can be differently controlled than a leg which is to perform a bending motion. Research has shown that during FES cycling substances are formed by the body that give a positive feeling. Especially a concentration present in the blood, of β-endorphin, the hormone par excellence capable of giving a feeling of pleasure during and after exercise, runs up substantially after 25 minutes of FES cycling.

The computer, preferably a palmtop, can be of detachable design, for instance to prevent theft.

Further, according to a preferred embodiment of the invention, the wheel of the reclining cycle is provided with a speed hub which preferably comprises an electric speed hub which changes gear automatically on the basis of a speed, such as, for instance, of the Shimano type. This provides the advantage that a rotational speed of the pedals can be adapted depending on a speed of the assembly.

Further, in a practical embodiment, the hand- or arm-drive can be adapted to be swung clear to facilitate a person sitting down in or getting up from the wheelchair. It is also possible that an orientation and/or position of a seat of the wheelchair relative to the rotatable shaft of the wheelchair is designed to be adjustable. This provides the advantage that a user of the wheelchair can optimize the seat for the activity in which the user is engaged in the wheelchair.

The invention further relates to a reclining cycle.

Further, the invention relates to a method for preventing muscular atrophy in at least one leg of an at least partly paralyzed person.

The invention will be further elucidated hereinbelow on the basis of a few embodiments represented in the drawing. In the drawing.

Figure 1:
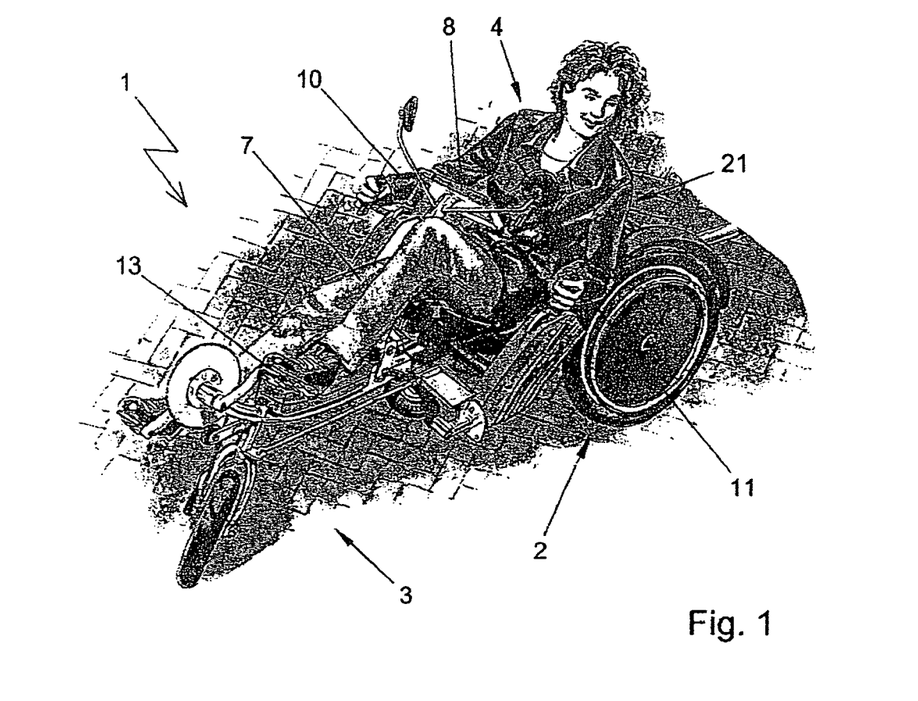
FIG. 1 is a side elevation (artist's impression) in oblique projection of a first embodiment of an assembly according to the invention, in use by a person such as, for instance, a paraplegic.

FIG. 1, being an artist's impression, represents a side elevation in oblique projection of the assembly 1, in a condition of use. The assembly 1 comprises a wheelchair 2 and a reclining cycle pan 3, allowing the paraplegic 4 to travel with an individually adjusted favorable setting of the seat 21 and the setting length of the connecting rube 6 of the reclining cycle part 3. The assembly 1, 101 is built up by coupling the wheelchair 2, 102 to the reclining cycle part 3, 103, the assembly being also drivable through cycling by way of at least one, preferably two, pedals. The pedals are coupled via a wheel or toothed wheel and a belt, rope or chain, to the wheel of the reclining cycle part. The coupling of wheelchair 2, 102 and reclining cycle part 3, 103 can comprise locking provision adapted to be uncoupled. The reclining cycle pan 3, 103 can comprise the front part of a specially designed reclining cycle or bicycle, the drive and steering being connected with, or coupled to, the front wheel 14. The leg muscles of the user 4, often a paraplegic, can be stimulated through electrodes from the electric energy source. The assembly further comprises an additional hand-/arm-drive 17 which is arranged by means of hub wheels or gear wheels with belts or chains on the wheelchair wheels, spring-mounted if desired, or the front wheel 14. Steering the assembly can be take place by tilting the hand- or arm-drive 17. The coupling of the reclining cycle part 3, 103 and the wheelchair 2, 102 is preferably adjustable and lockable by means of tubes, one sliding into other, with bores and locking means. On a console 20 which is preferably adapted to be swung clear, a computer 8 is arranged for controlling the electrodes. The assembly is further provided with an electric energy source for ElectroStimulation of a cycling motion at the legs.

Figure 15:
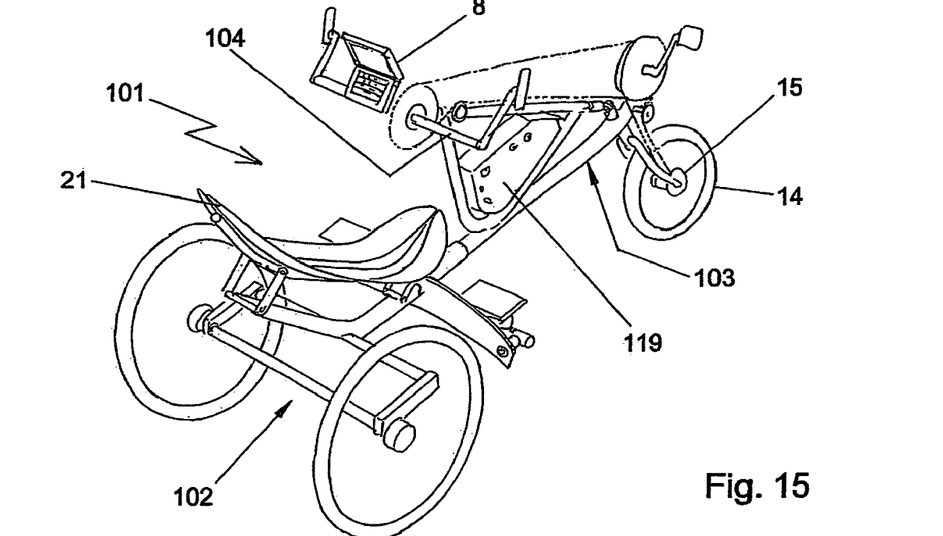
FIGS. 15–17 show, in oblique projection, a second embodiment of an assembly according to the invention.

The hand-/arm-drive 17, 104 is built up from at least one special handle-pedal construction with belt, rope and chain drive on, if desired, an intermediate shaft, which, by means of belt, rope or chain, is coupled to transmission means on the rear axle of the wheelchair 2, 102.

The belt, rope or chain drive can be connected to the rear axle of the wheelchair 2, 102 via a derailleur/speed-changing gear with differential 22. On the rear axle, further, an auxiliary motor may be mounted.

The special speed hub 15 can be an automatic gear-shifting electric speed hub, as of the Sachs/Shimano type, which changes gear itself, depending on the speed.

The seat 21 of the wheelchair 2, 102 is designed as a reclining element of a reclining cycle, which reclining element may be provided at the bottom with a lockable double rod system for setting the desired position for the user.

Figure 2:
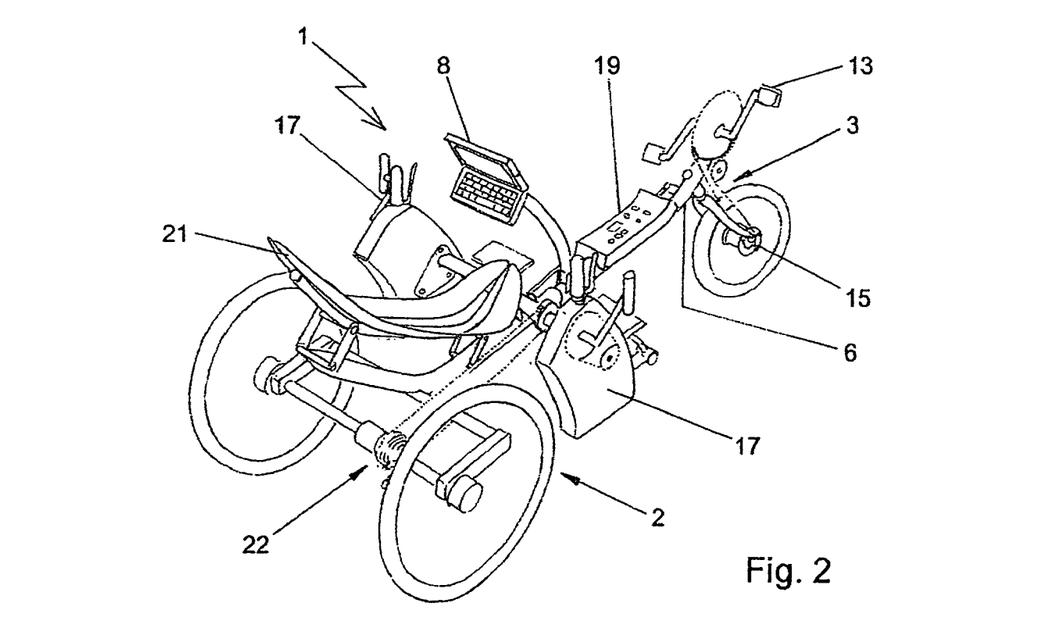
FIG. 2 is an oblique projection taken from a different angle, of the same embodiment as represented in FIG. 1.

In FIG. 2 the various parts of the assembly 1 are shown in more detail. To enable cycling, Functional ElectroStimulation (FES) is to be fitted to the leg muscles of the paraplegic 4. The electrodes for stimulation can be fitted in special trousers 7 of the paraplegic and be controlled by the laptop or palmtop 8 coupled to the FES electronics unit 19.

According to one embodiment, the assembly according to the invention has been developed further, such that the complete activation of the leg muscles of the user takes place with the aid of an incremental pedal angle gauge which transmits the position of the crank set or pedal assembly to the computer (laptop or palmtop). The computer regulates, with an FES system known per se, which muscles are to be controlled at any time. The electrodes, which can be fitted in fitting custom-made trousers for the user, constitute the connection between the leg muscles and the electric energy source. The electric energy source is preferably included in the electronics unit. In a safe embodiment, if the hand brake is squeezed, stimulation of the leg muscles stops.

The deficit of driving power, which will certainly be present in the initial phase of putting the assembly into operation, is compensated by the arms 10 and 11. The assembly in coupled condition can comprise a three-wheel cycle. A part thereof, viz the wheelchair, can, after uncoupling of the reclining cycle part, also be used solely as wheelchair. Most users of the assembly will be able to cover large distances and attain high speeds in that the legs, by virtue of the FES, can make a positive contribution to the propulsion of the assembly. For instance for paraplegics, the assembly of wheelchair 2 and reclining cycle part 3 can be an appliance of daily use, allowing the patient to go shopping, to visit friends, and even to go on a cycling holiday.

Figure 3:
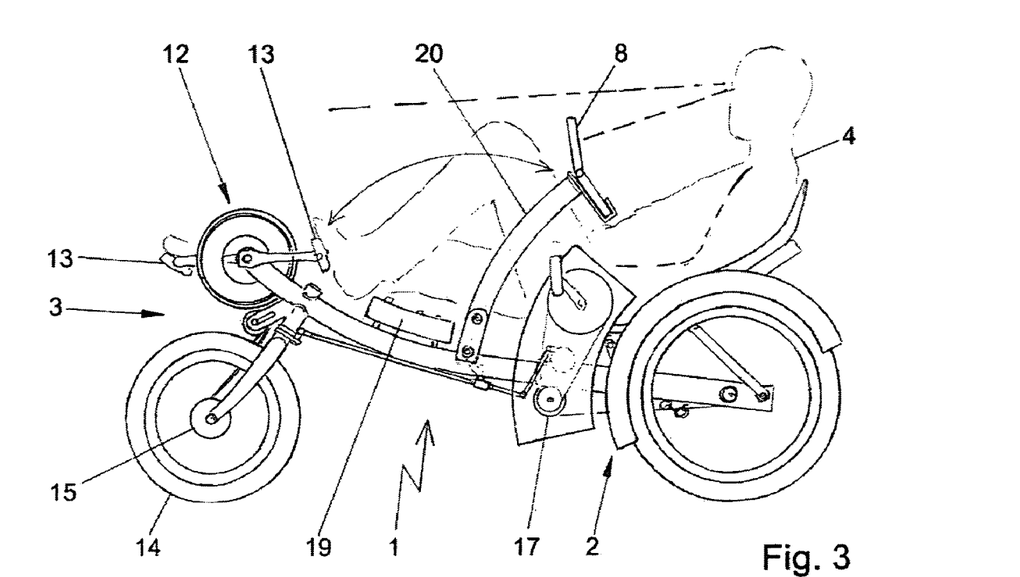
FIGS. 3–8 show various views of the first embodiment to represent the use, the uncoupling of the reclining cycle part and the wheelchair, the steering and the setting of the seat part of the wheelchair.
Figure 6:
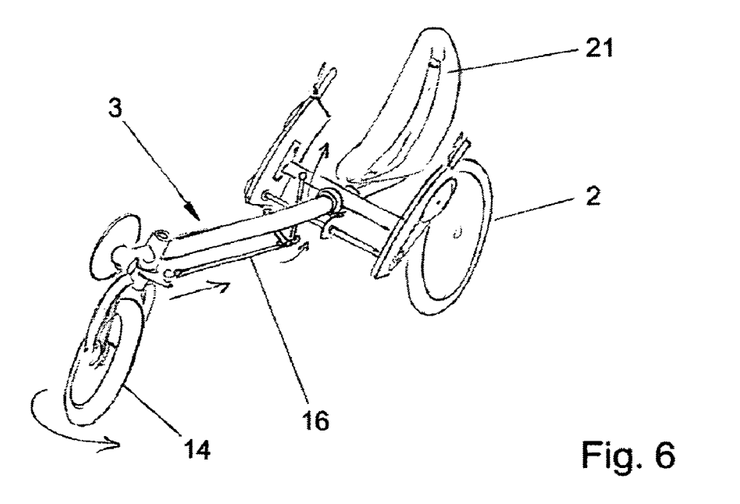
Figure 7:
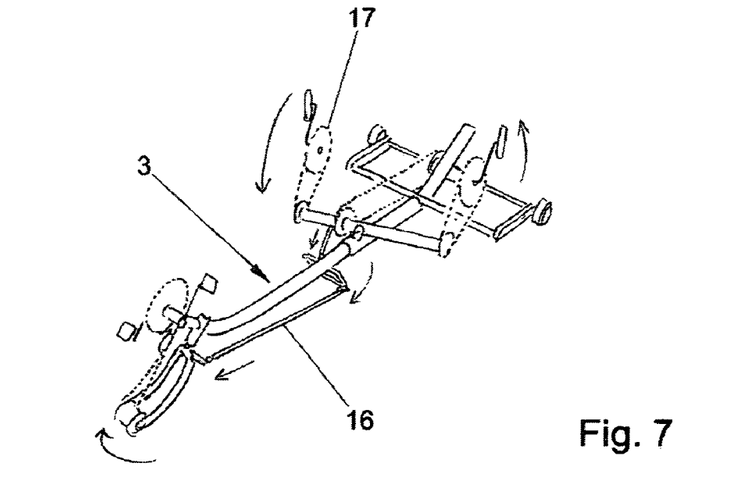

In FIG. 3 the assembly 1 is represented together with a cycling paraplegic 4. The drive 12 with the pedals 13 is arranged on the front wheel 14, which may typically be provided with an (automatic) speed hub 15. The actual steering is done by tilting the so-called arm-/hand-drive 17 (see especially FIG. 7). This steering of the front wheel 14 is done by transmitting the tilt via the rod system 16, which is also represented in FIGS. 6 and 7.

Figure 4:
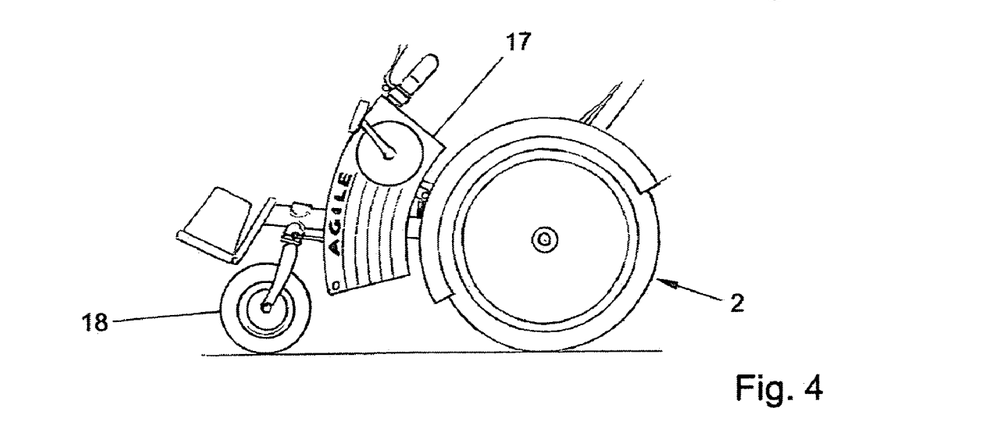
Figure 5:
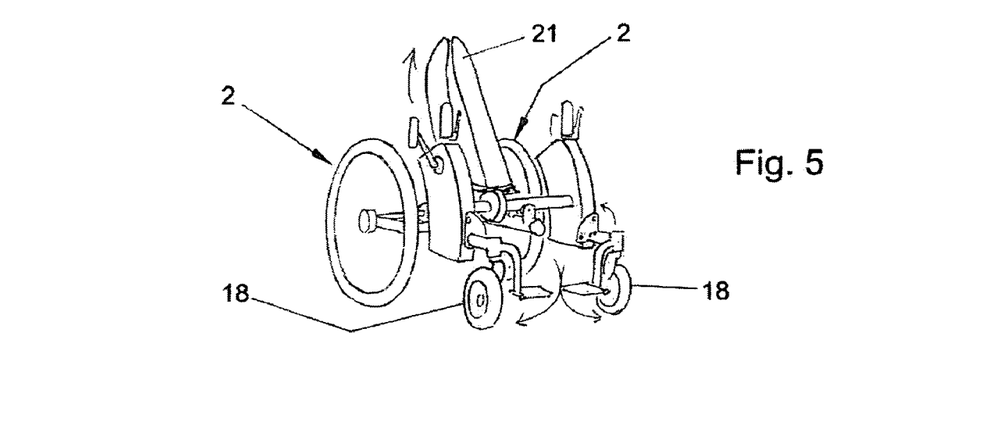
Figure 8:
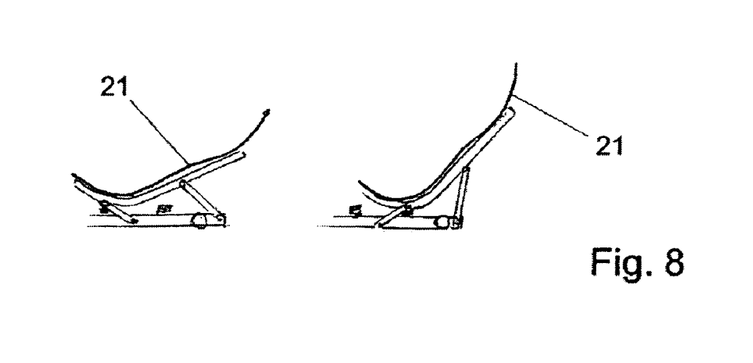
Figure 9:
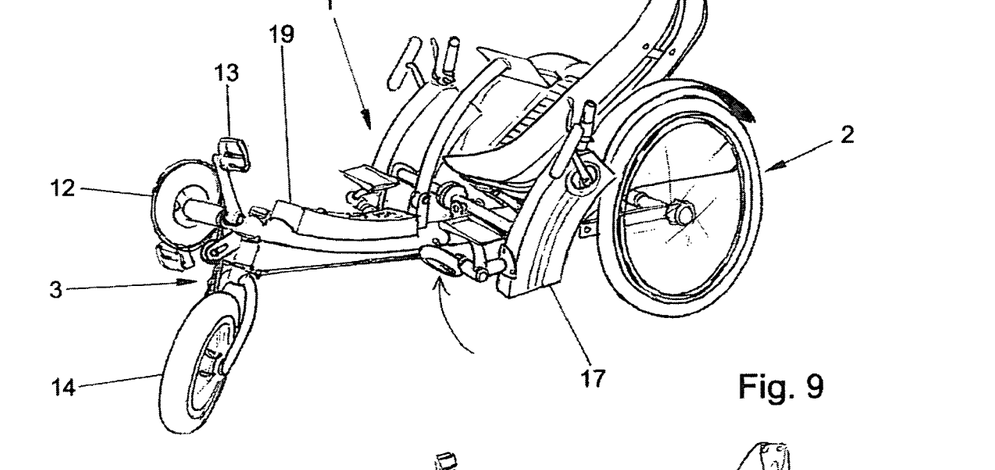
FIGS. 9–14 show, from various viewpoints, an oblique projection of the different parts of the assembly according to the first embodiment, for further clarification of the operation thereof.
Figure 10:
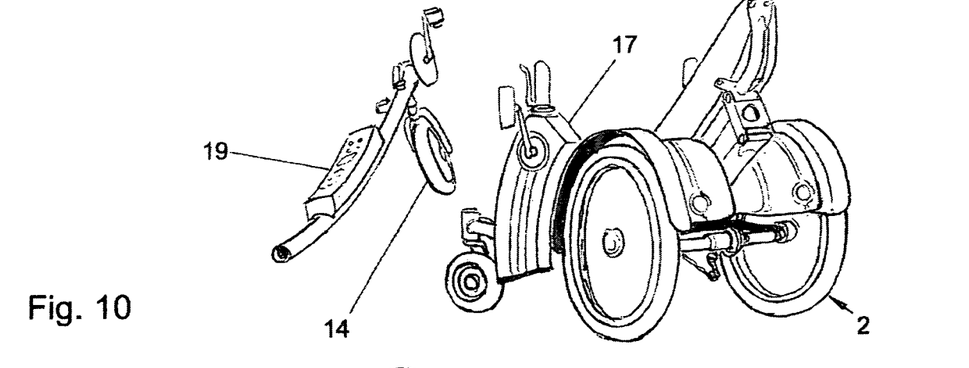
Figure 11:
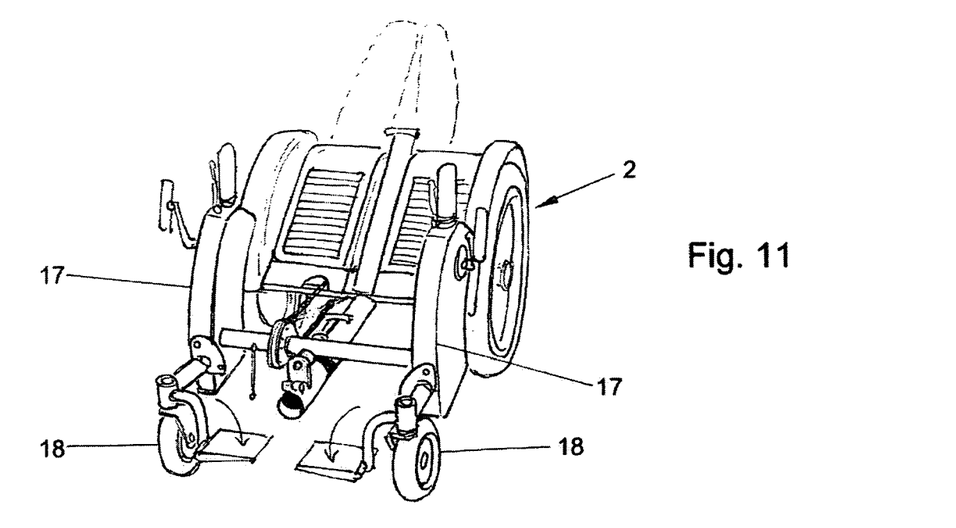
Figure 12:
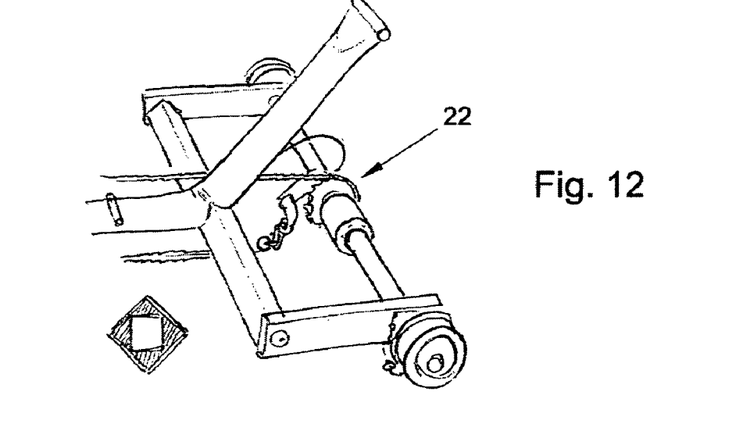

In FIG. 4 the arm-/hand-drive 17 is clearly represented in side view with the wheelchair 2 uncoupled. In this condition, the wheels 18 of the wheelchair 2 are swung outwards for use (see also FIG. 5). In FIG. 3, further, the Functional ElectroStimulation (FES) system 19 and the laptop or palmtop 8 are fitted on the hinged console 20. The patient 4 is sitting on an adjustable seat 21 on the-wheelchair 2 (see also FIG. 8).

Figure 13:
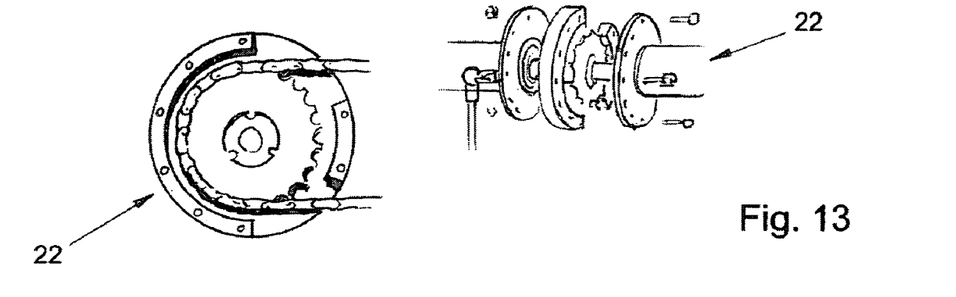
Figure 14:
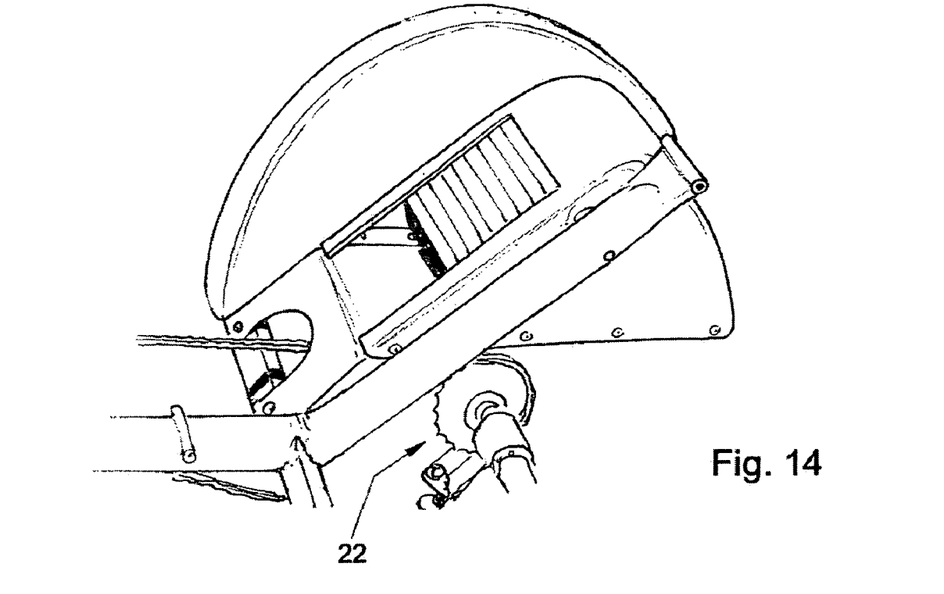

In FIGS. 9 to 14, for clarification, various parts of the apparatus or the assembly 1 are represented; in FIG. 13 the differential 22. Further, the details in the various figures are self-explanatory.

Figure 16:
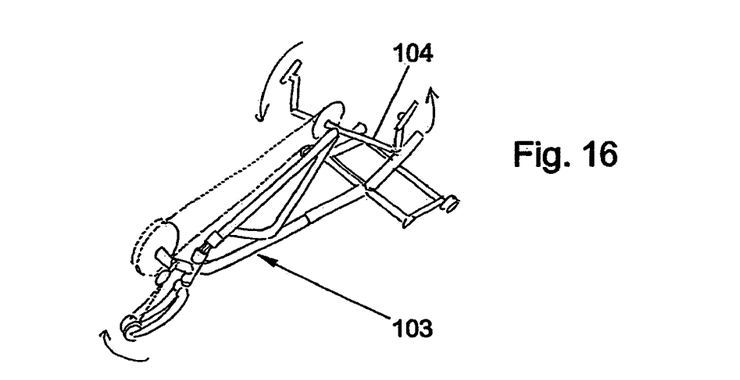
Figure 17:
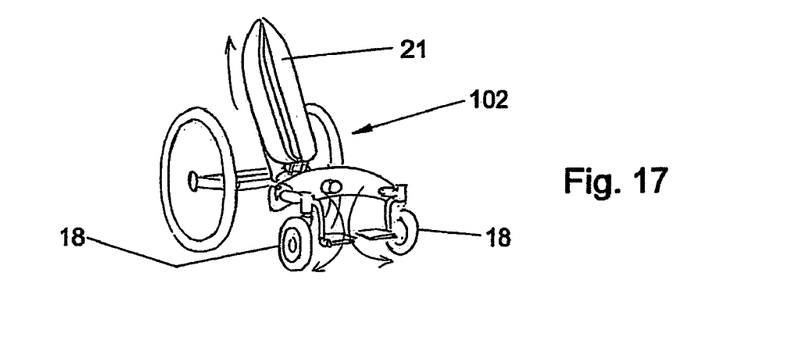

In FIGS. 15 to 17, in oblique projection, a second embodiment of the assembly 10 with the wheelchair 102 and the reclining cycle pan 103 is represented. The hand- or arm-drive 17, 104 is built up from at least one special handle-pedal construction with belt, rope or chain drive connected to the drive of the front wheel 14 mentioned. The FES system 119 is conveniently incorporated between the frame of the reclining cycle part 103. The laptop or palmtop 8 is now mounted adjacent the steering rod/drive rod with arm-/hand-drive 104. Steering of the front wheel 14 is effected by tilting and/or by turning as with a handlebar of an ordinary bicycle. The steering of the whole is indicated, by way of example, in FIG. 16. Preparing the wheelchair 102 is represented in FIG. 17.

The invention is not limited in any way to the examples discussed. Many variants and modifications are possible. Instead of the hand- or arm-drive, the separate drive can also comprise an electric moton Also, the wheel of the reclining cycle pan can be placed on a running belt or be otherwise included in a home trainer. The handlebar can be of adjustable design to facilitate sitting down in and getting up from the wheelchair. Moreover, in that case, also the position of the handlebar can be optimized in view of the length of the arms and possibly the legs of the user of the assembly. Also, the coupling of the wheelchair to the reclining cycle part can be designed such that the assembly can be made suitable for virtually any user, independently of the height of the user. The hand- or arm-drive and the leg-drive can be adjusted such that a user, during the cycling motion and while using the hand- or arm-drive, does not have one of his arms butting against one of his legs. At various positions, such as, for instance, in the wheel of the reclining cycle part, the assembly can be provided with a so-called freewheel, so that the wheel can rotate without being driven. This can be convenient, for instance, when the user is traveling downhill with the assembly. Obviously, the assembly can also be used without using the electric energy source. In that case, the drive takes place with the aid of the separate drive. The assembly can be provided with various designs of a brake, such as, for instance, on the wheelchair wheels and on the handlebar These can be coupled to the computer and/or the electric energy source.

A skilled person will preferably include belt or chain tensioners at various points in the assembly. The wheelchair can be provided with a double rear axle, so that, if desired, the rear wheels can be displaced. The pedals will preferably be provided with self-locking means for holding a leg on the pedal. To be considered here are, for instance, closures such as are used on a snowboard or a ski fastening. Also applicable are simpler means for keeping a leg on the pedal, such as, for instance, a strap and/or a frame in the form of a shoe. The wheels of the wheelchair are preferably provided with hoops, so that the user can also travel in the conventional manner, without the reclining cycle part.

Naturally, in cases where an electric motor is fitted on the wheelchair, the electric motor can also be used when the reclining cycle part is uncoupled from the wheelchair.

Especially paraplegics who, due to the incomplete regulation of the intestines, suffer more often from problems such as: poor condition, cardiovascular diseases, diabetes, digestive disorders, decubitus ulcers, leg muscle spasms, leg muscle atrophy, osteoporosis, and poor circulation in the legs, can benefit greatly from the invention.

The costs of transport, rehabilitation and health care can be reduced with the aid of the invention, and users of the assembly can come out of their isolation, for instance, by participating in public traffic.

Although in the foregoing the handlebar of the assembly has been shown as a manually steerable handlebar, the invention is not limited to the use of such a conventional handlebar. The handlebar can also comprise, for instance, a control stick which is operable, for instance, by hand or through a motion of the head. Instead of, or in addition to, a manually steerable handlebar, the assembly may also include a steering facility which is steerable through, for instance, speech recognition or eye movement.

The wheelchair and the reclining cycle part can also be integrated with each other in the assembly. Such variants are all understood to fall within the invention.

The invention claimed is:

1. An assembly comprising:
   a wheelchair,
   a reclining cycle portion,
   a coupling connecting the wheelchair and the reclining cycle portion,
   wherein the reclining cycle portion comprises:
      a wheel, and
      at least one foot pedal driving the wheel when coupled,
      a handlebar connected with the wheel of the reclining cycle portion, wherein the handlebar steers the assembly,
      wherein the at least one foot pedal is coupled to the wheel of the reclining cycle portion with a first drive, and wherein the first drive is arranged to rotate in a predetermined plane irrespective the position of the steerable wheel; and
      a second drive coupled with the wheel of the reclining cycle portion, the second drive comprising a hand- or arm- drive attached to the handlebar, wherein the hand- or arm- drive comprises at least one manually drivable pedal driving the wheel of the reclining cycle portion by a drive shaft and chains or belts.

2. The assembly of claim 1, wherein the assembly further comprising an electric energy source for electrostimulation.

3. A reclining cycle portion for an assembly having a wheelchair, a reclining cycle portion, and a coupling, wherein the coupling connects the wheelchair and the reclining cycle portion, wherein the reclining cycle portion comprises:
   a wheel;
   at least one foot pedal;
   a pedal coupling, the pedal coupling connecting the wheel to the foot pedal and having a first drive;
   wherein the pedal drives the wheel of the reclining cycle portion, and wherein when coupled, the assembly is propelled by a person in the wheelchair from cycling motion of the person's leg against the foot pedal;
   a handlebar connected with the wheel of the reclining cycle portion, the handlebar steering the assembly;
   wherein the first drive is arranged to rotate in a predetermined plane with respect to the reclining portion irrespective of the position of the steerable wheel;
   wherein the reclining cycle portion further comprises a second drive coupled with the wheel of the reclining cycle portion, the second drive comprising a hand- or arm-drive attached to the handlebar, wherein the hand- or arm-drive comprises at least one manually drivable pedal, a drive shaft, and chains or belts, and wherein the drivable pedal drives the wheel of the reclining cycle portion.

4. An assembly comprising:
   a wheelchair,
   a reclining cycle portion,
   a first coupling connecting the wheelchair and the reclining cycle portion,
   wherein the reclining cycle portion comprises:
      a wheel, and
      at least one foot pedal driving the wheel when coupled,
      a handlebar connected with the wheel of the reclining cycle portion, wherein the handlebar steers the assembly,
      wherein the at least one foot pedal is coupled to the wheel of the reclining cycle portion with a second coupling including a first drive, and wherein the first drive is arranged to rotate in a predetermined plane irrespective the position of the steerable wheel, and wherein the second coupling includes a drive element extending from the first drive to the wheel, the drive element being selected from the group consisting of: a toothed wheel, a belt, a rope or chain; and
      a second drive coupled with the wheel of the reclining cycle portion, the second drive comprising a hand- or arm- drive attached to the handlebar, wherein the hand- or arm- drive comprises at least one manually drivable pedal driving the wheel of the reclining cycle portion by a drive shaft and chains or belts.

5. An assembly comprising:
a wheelchair,
a reclining cycle portion,
wherein the reclining cycle portion comprises:
   a wheel, and
   at least one foot pedal driving the wheel when coupled,
   a handlebar connected with the wheel of the reclining cycle portion, wherein the handlebar steers the assembly,
   wherein the at least one foot pedal is coupled to the wheel of the reclining cycle portion with a coupling including a first drive, and wherein the first drive is arranged to rotate in a predetermined plane irrespective the position of the steerable wheel, and wherein the coupling includes a drive element extending from the first drive to the wheel, the drive element being selected from the group consisting of: a toothed wheel, a belt, a rope or chain; and
a second drive coupled with the wheel of the reclining cycle portion, the second drive comprising a hand- or arm- drive attached to the handlebar, wherein the hand- or arm- drive comprises at least one manually drivable pedal driving the wheel of the reclining cycle portion by a drive shaft and chains or belts.

* * * * *